(12) United States Patent
Sponholtz, III

(10) Patent No.: US 10,149,830 B2
(45) Date of Patent: Dec. 11, 2018

(54) PHARMACEUTICAL AGENTS AND METHODS RELATING THERETO

(71) Applicant: Cushing Academy, Ashburnham, MA (US)

(72) Inventor: William R. Sponholtz, III, Marion, NC (US)

(73) Assignee: Cushing Academy, Ashburnham, MA (US)

( * ) Notice: Subject to any disclaimer, the term of this patent is extended or adjusted under 35 U.S.C. 154(b) by 0 days.

(21) Appl. No.: 15/606,503

(22) Filed: May 26, 2017

(65) Prior Publication Data

US 2017/0348279 A1 Dec. 7, 2017

Related U.S. Application Data

(60) Provisional application No. 62/345,302, filed on Jun. 3, 2016.

(51) Int. Cl.
*A61K 31/366* (2006.01)
*A61K 45/06* (2006.01)

(52) U.S. Cl.
CPC .......... *A61K 31/366* (2013.01); *A61K 45/06* (2013.01)

(58) Field of Classification Search
CPC .................................................. A61K 31/366
USPC ....................................................... 514/460
See application file for complete search history.

(56) References Cited

U.S. PATENT DOCUMENTS

2001/0031763 A1  10/2001  Steiner

FOREIGN PATENT DOCUMENTS

| DE | 19826499 | * | 6/1998 | ............... A61K 7/40 |
| WO | WO-94/07887 A1 | | 4/1994 | |
| WO | WO-2007/068498 A1 | | 6/2007 | |

OTHER PUBLICATIONS

Rolli,Chem. Biodiversity, 2016, 13, 66-76.*
Wickel European Journal of Organic Chemistry (2013), 2013(14), 2906-2913.*
Králové, H., Monosubstituted 5,6-dihydro-2H-pyran-2-ones. Natural occurrence, biological activity and synthetic approaches, RIGOROUS Thesis, Mgr. Petr Bešťák, Univerzita Karlova V Praze, 58 pages (2009).
Barros, M.E.S.B. et al., Synthesis and evaluation of (−)-Massoialactone and analogues as potential anticancer and anti-inflammatory agents, European Journal of Medicinal Chemistry, 76: 291-300 (2014).
Damia, G. and D'Incalci, M., Contemporary pre-clinical development of anticancer agents—What are the optimal preclinical models?, European Journal of Cancer, 45: 2768-2781 (2009).
De Clercq, P. et al., The Total Synthesis of Fragrant Compounds from Jasmine Oil, Bull. Soc. Chim. Belg., 87(6): 495-496 (1978).
De Fátima, A. et al., Styryl Lactones and Their Derivatives: Biological Activities, Mechanisms of Action and Potential Leads for Drug Design, Current Medicinal Chemistry, 13: 3371-3384 (2006).
Dubs, P. and Stussi, R., Partial syntheses of methyl dehydrojasmonate and tuberolactone, Helv. Chim. Acta, 61(3):998-1003 (1978).
Fang, S. et al., A new essential oil component from Datura stramonium, Chinese Traditional and Herbal Drugs, 44:2035-2038 (2013). English Abstract.
Fehr, C. et al., 115. Novel Approach to the Synthesis of 6-Substituted 5,6-Dihydro-2 (2H)-pyranones, Helv. Chim. Acta, 64(5):1247-1256 (1981).
Johnson, J. et. al., Relationships between drug activity in NCI preclinical in vitro and in vivo models and early clinical trials. British Journal of Cancer, 84: 1424-1431 (2001).
Kaiser, R. and Lamparsky, D., Das lacton der 5-hydroxy-cis-2,cis-7-decadiensaeure and weitere lactone aus dem absolue der blueten von polianthes tuberosa L, Tetrahedron Lett., 20: 1659-1660 (1976). No Known English Language Copy.
Kaiser, R. and Lamparsky, D., Volatile Constituents of Osmanthus Absolute, Essential Oils, A symposium sponsored by the Division of Agricultural and Food Chemistry at the 178th Meeting of the American Chemical Society, Washington, DC, 36 pages. (Sep. 12, 1979).
Ocana, A., et al., Preclinical development of molecular targeted agents for cancer, Nat. Rev. Clin. Oncol., 8: 200-209 (2011).
Sabitha, G. et al., The first asymmetric total synthesis of (R)-tuberolactone, (S)-jasmine lactone and (R)-δ-decalactone, Tetrahedron, 47:8179-8181 (2006).
Sharma, S. V., et al., Cell line-based platforms to evaluate the therapeutic efficacy of candidate anticancer agents, Nature Reviews Cancer, 10: 241-253 (2010).
Venkatesh, S. and Lipper, R. A., Role of the Development Scientist in Compound Lead Selection and Optimization, Journal of Pharmaceutical Sciences, 89(2):145-154 (2000).

* cited by examiner

*Primary Examiner* — Nizal S Chandrakumar
(74) *Attorney, Agent, or Firm* — Choate, Hall & Stewart LLP; Brenda Herschbach Jarrell

(57) ABSTRACT

The instant disclosure is related to lactone-containing compounds of formula (I), compositions thereof, and use thereof for treating proliferative disease or disorders. Also provided herein are methods of making, identifying, or characterizing the compounds, or compositions thereof.

10 Claims, No Drawings

PHARMACEUTICAL AGENTS AND METHODS RELATING THERETO

CROSS REFERENCE TO RELATED APPLICATIONS

The present application claims priority to U.S. provisional patent application Ser. No. 62/345,302, filed Jun. 3, 2016, the entire content of which is hereby incorporated by reference.

BACKGROUND

Undesirable cell proliferation contributes to a variety of diseases, disorders, and conditions, including for example, cancer, autoimmune diseases, inflammatory disorders, microbial infections, etc. (collectively "proliferative conditions"). Effective anti-proliferative agents have great utility in various contexts.

SUMMARY

The present disclosure describes identification and characterization of certain compounds of interest, and particularly of certain compounds with antiproliferative activities. The present disclosure provides, among other things, compositions comprising such compounds, and also methods of making, using, identifying and/or characterizing such compounds (and/or compositions containing them). Particularly provided herein are methods for treating one or more proliferative conditions using a compound or composition as described herein.

In some embodiments, provided herein is a method for treating a proliferative condition in a subject in need thereof, comprising administering to the subject a therapeutically effective amount of a compound of formula (I):

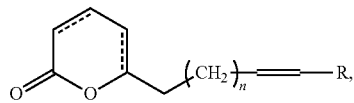

(I)

wherein:
each of ----- is independently absent or a bond;
n is 0-6; and
R is $C_{1-6}$ alkyl, which is optionally substituted 1-3 times by halo, hydroxyl, or $C_{1-6}$ alkoxy.

In some embodiments, provided herein is a method for making a compound of formula (I), comprising a step of obtaining from a plant an extract comprising the compound of formula (I), wherein:
each of ----- is independently absent or a bond;
n is 0-6; and
R is $C_{1-6}$ alkyl, which is optionally substituted 1-3 times by halo, hydroxyl, or $C_{1-6}$ alkoxy.

In some embodiments, provided herein is a method for identifying or characterizing an antiproliferative compound, the method comprising steps of:
testing a plurality of samples, each of which is derived from a plant for antiproliferative activity; and
determining that at least one sample with detectable antiproliferative activity comprises a compound of formula (I), wherein:
each of ----- is independently absent or a bond;
n is 0-6; and
R is $C_{1-6}$ alkyl, which is optionally substituted 1-3 times by halo, hydroxyl, or $C_{1-6}$ alkoxy.

In some embodiments, provided herein is a method for formulating a pharmaceutical composition, the method comprising a step of combining one or more pharmaceutically acceptable carriers or excipients with a compound of formula (I), wherein:
each of ----- is independently absent or a bond;
n is 0-6; and
R is $C_{1-6}$ alkyl, which is optionally substituted 1-3 times by halo, hydroxyl, or $C_{1-6}$ alkoxy.

In some embodiments, provided herein is a method of identifying and/or characterizing a composition comprising a formula (I), the method comprising a step of assessing antiproliferative activity of the composition, wherein:
each of ----- is independently absent or a bond;
n is 0-6; and
R is $C_{1-6}$ alkyl, which is optionally substituted 1-3 times by halo, hydroxyl, or $C_{1-6}$ alkoxy.

DETAILED DESCRIPTION OF CERTAIN EMBODIMENTS

Definitions

Definitions of specific functional groups and chemical terms are described in more detail below. For purposes of this disclosure, chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito: 1999, the entire contents of which are incorporated herein by reference.

Administration: As used herein, the term "administration" typically refers to the administration of a composition to a subject or system. Those of ordinary skill in the art will be aware of a variety of routes that may, in appropriate circumstances, be utilized for administration to a subject, for example a human. For example, in some embodiments, administration may be ocular, oral, parenteral, topical, etc. In some particular embodiments, administration may be bronchial (e.g., by bronchial instillation), buccal, dermal (which may be or comprise, for example, one or more of topical to the dermis, intradermal, interdermal, transdermal, etc.), enteral, intra-arterial, intradermal, intragastric, intramedullary, intramuscular, intranasal, intraperitoneal, intrathecal, intravenous, intraventricular, within a specific organ (e.g. intrahepatic), mucosal, nasal, oral, rectal, subcutaneous, sublingual, topical, tracheal (e.g., by intratracheal instillation), vaginal, vitreal, etc. In some embodiments, administration may involve dosing that is intermittent (e.g., a plurality of doses separated in time) and/or periodic (e.g., individual doses separated by a common period of time) dosing. In some embodiments, administration may involve continuous dosing (e.g., perfusion) for at least a selected period of time.

Analog: As used herein, the term "analog" refers to a substance that shares one or more particular structural features, elements, components, or moieties with a reference substance. Typically, an "analog" shows significant structural similarity with the reference substance, for example sharing a core or consensus structure, but also differs in certain discrete ways. In some embodiments, an analog is a substance that can be generated from the reference substance, e.g., by chemical manipulation of the reference substance. In some embodiments, an analog is a substance that can be generated through performance of a synthetic process substantially similar to (e.g., sharing a plurality of steps with) one that generates the reference substance. In some embodiments, an analog is or can be generated through performance of a synthetic process different from that used to generate the reference substance.

Associated with: Two events or entities are "associated" with one another, as that term is used herein, if the presence, level and/or form of one is correlated with that of the other. For example, a particular entity (e.g., polypeptide, genetic signature, metabolite, microbe, etc) is considered to be associated with a particular disease, disorder, or condition, if its presence, level and/or form correlates with incidence of and/or susceptibility to the disease, disorder, or condition (e.g., across a relevant population). In some embodiments, two or more entities are physically "associated" with one another if they interact, directly or indirectly, so that they are and/or remain in physical proximity with one another. In some embodiments, two or more entities that are physically associated with one another are covalently linked to one another; in some embodiments, two or more entities that are physically associated with one another are not covalently linked to one another but are non-covalently associated, for example by means of hydrogen bonds, van der Waals interaction, hydrophobic interactions, magnetism, and combinations thereof.

Bacterial infection: The term "bacterial infection," as used herein, refers to a disease or condition that is caused by and/or associated or correlated with presence and/or proliferation of bacterial cells. In some embodiments, relevant bacterial cells are gram-(−); in some embodiments, relevant bacterial cells are gram-(+).

Cancer: The terms "cancer", "malignancy", "neoplasm", "tumor", and "carcinoma", are used herein to refer to cells that exhibit relatively abnormal, uncontrolled, and/or autonomous growth, so that they exhibit an aberrant growth phenotype characterized by a significant loss of control of cell proliferation. In some embodiments, a tumor may be or comprise cells that are precancerous (e.g., benign), malignant, pre-metastatic, metastatic, and/or non-metastatic. The present disclosure specifically identifies certain cancers to which its teachings may be particularly relevant. In some embodiments, a relevant cancer may be characterized by a solid tumor. In some embodiments, a relevant cancer may be characterized by a hematologic tumor. In general, examples of different types of cancers known in the art include, for example, hematopoietic cancers including leukemias, lymphomas (Hodgkin's and non-Hodgkin's), myelomas and myeloproliferative disorders; sarcomas, melanomas, adenomas, carcinomas of solid tissue, squamous cell carcinomas of the mouth, throat, larynx, and lung, liver cancer, genitourinary cancers such as prostate, cervical, bladder, uterine, and endometrial cancer and renal cell carcinomas, bone cancer, pancreatic cancer, skin cancer, cutaneous or intraocular melanoma, cancer of the endocrine system, cancer of the thyroid gland, cancer of the parathyroid gland, head and neck cancers, breast cancer, gastro-intestinal cancers and nervous system cancers, benign lesions such as papillomas, and the like.

Combination therapy: As used herein, the term "combination therapy" refers to those situations in which a subject is simultaneously exposed to two or more therapeutic regimens (e.g., two or more therapeutic agents). In some embodiments, the two or more regimens may be administered simultaneously; in some embodiments, such regimens may be administered sequentially (e.g., all "doses" of a first regimen are administered prior to administration of any doses of a second regimen); in some embodiments, such agents are administered in overlapping dosing regimens. In some embodiments, "administration" of combination therapy may involve administration of one or more agents or modalities to a subject receiving the other agents or modalities in the combination. For clarity, combination therapy does not require that individual agents be administered together in a single composition (or even necessarily at the same time), although in some embodiments, two or more agents, or active moieties thereof, may be administered together in a combination composition, or even in a combination compound (e.g., as part of a single chemical complex or covalent entity).

Comparable: As used herein, the term "comparable" refers to two or more agents, entities, situations, sets of conditions, etc., that may not be identical to one another but that are sufficiently similar to permit comparison therebetween so that one skilled in the art will appreciate that conclusions may reasonably be drawn based on differences or similarities observed. In some embodiments, comparable sets of conditions, circumstances, individuals, or populations are characterized by a plurality of substantially identical features and one or a small number of varied features. Those of ordinary skill in the art will understand, in context, what degree of identity is required in any given circumstance for two or more such agents, entities, situations, sets of conditions, etc. to be considered comparable. For example, those of ordinary skill in the art will appreciate that sets of circumstances, individuals, or populations are comparable to one another when characterized by a sufficient number and type of substantially identical features to warrant a reasonable conclusion that differences in results obtained or phenomena observed under or with different sets of circumstances, individuals, or populations are caused by or indicative of the variation in those features that are varied.

Dosage form or unit dosage form: Those skilled in the art will appreciate that the term "dosage form" may be used to refer to a physically discrete unit of an active agent (e.g., a therapeutic or diagnostic agent) for administration to a subject. Typically, each such unit contains a predetermined quantity of active agent. In some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen). Those of ordinary skill in the art appreciate that the total amount of a therapeutic composition or agent administered to a particular subject is determined by one or more attending physicians and may involve administration of multiple dosage forms.

Dosing regimen: Those skilled in the art will appreciate that the term "dosing regimen" may be used to refer to a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which is separated in time from other doses. In some embodiments, individual doses are separated from one another by a time period of the same length; in some embodiments, a dosing regimen comprises a plurality of doses and at least two different time periods separating individual doses. In some embodiments, all doses within a dosing regimen are of the same unit dose amount.

In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount In some embodiments, a dosing regimen is correlated with a desired or beneficial outcome when administered across a relevant population (i.e., is a therapeutic dosing regimen).

Isomer: As is known in the art, many chemical entities (in particular many organic molecules and/or many small molecules) can exist in a variety of structural (e.g., geometric, conformational, isotopic) and/or optical isomeric forms. For example, any chiral center can exist in R and S configurations, double bonds can exist in Z and E conformational isomers, certain structural elements can adopt two or more tautomeric forms, certain structures can be substituted with one or more isotopically enriched atoms (e.g., deuterium or tritium for hydrogen, $^{12}C$ or $^{14}C$ for $^{13}C$, $^{131}I$ for $^{129}I$, etc.). In some embodiments, as will be clear to those skilled in the art from context, depiction of or reference to a particular compound structure herein may represent all structural and/or optical isomers thereof. In some embodiments, as will be clear to those skilled in the art from context, depiction of or reference to a particular compound structure herein is intended to encompass only the depicted or referenced isomeric form. In some embodiments, compositions including a chemical entity that can exist in a variety of isomeric forms include a plurality of such forms; in some embodiments such compositions include only a single form. For example, in some embodiments, compositions including a chemical entity that can exist as a variety of optical isomers (e.g., stereoisomers, diastereomers, etc.) include a racemic population of such optical isomers; in some embodiments such compositions include only a single optical isomer and/or include a plurality of optical isomers that together retain optical activity.

Marker: A marker, as used herein, refers to an entity or moiety whose presence or level is a characteristic of a particular state or event. In some embodiments, presence or level of a particular marker may be characteristic of presence or stage of a disease, disorder, or condition. To give but one example, in some embodiments, the term refers to a gene expression product that is characteristic of a particular tumor, tumor subclass, stage of tumor, etc. Alternatively or additionally, in some embodiments, a presence or level of a particular marker correlates with activity (or activity level) of a particular signaling pathway, for example that may be characteristic of a particular class of tumors. The statistical significance of the presence or absence of a marker may vary depending upon the particular marker. In some embodiments, detection of a marker is highly specific in that it reflects a high probability that the tumor is of a particular subclass. Such specificity may come at the cost of sensitivity (i.e., a negative result may occur even if the tumor is a tumor that would be expected to express the marker). Conversely, markers with a high degree of sensitivity may be less specific that those with lower sensitivity. According to the present invention a useful marker need not distinguish tumors of a particular subclass with 100% accuracy.

Parenteral: The terms "parenteral administration" and "administered parenterally," as used herein, refer to modes of administration other than enteral and topical administration, usually by injection. In some embodiments, parenteral administration may be or comprise intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and/or infusion.

Patient: As used herein, the term "patient" refers to any organism to which a provided composition is or may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. In some embodiments, a patient is suffering from or susceptible to one or more disorders or conditions. In some embodiments, a patient displays one or more symptoms of a disorder or condition. In some embodiments, a patient has been diagnosed with one or more disorders or conditions. In some embodiments, the disorder or condition is or includes cancer, or presence of one or more tumors. In some embodiments, the patient is receiving or has received certain therapy to diagnose and/or to treat a disease, disorder, or condition.

Pharmaceutical composition: As used herein, the term "pharmaceutical composition" refers to a composition in which an active agent is formulated together with one or more pharmaceutically acceptable carriers. In some embodiments, the active agent is present in unit dose amount appropriate for administration in a therapeutic regimen that shows a statistically significant probability of achieving a predetermined therapeutic effect when administered to a relevant population. In some embodiments, a pharmaceutical composition may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces. Those skilled in the art will appreciate that, in general, any composition that is formulated for administration to a human or animal subject, may, in some embodiments, be considered to be a pharmaceutical composition, whether or not its administration requires a medical prescription. Thus, for example, in some embodiments, a food or food supplement composition (e.g., a liquid or solid consumable composition such as a shake or sports drink or nutritional supplement powder) may be considered to be a pharmaceutical composition. Alternatively or additionally, in some embodiments, a pharmaceutical composition may be a formulation that is specifically regulated and approved for administration to relevant subjects by an appropriate government agency such as, for example, the Food and Drug Administration in the United States. In some embodiments, a pharmaceutical composition is one that cannot legally be administered without a prescription from a licensed medical practitioner.

Pharmaceutically acceptable: As used herein, the term "pharmaceutically acceptable" applied to a carrier, diluent, or excipient used to formulate a composition as disclosed herein means that the carrier, diluent, or excipient must be compatible with the other ingredients of the composition and not deleterious to the recipient thereof.

Pharmaceutically acceptable carrier: As used herein, the term "pharmaceutically acceptable carrier" means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Prevent or prevention: as used herein when used in connection with the occurrence of a disease, disorder, and/or condition, refers to reducing the risk of developing the disease, disorder and/or condition and/or to delaying onset of one or more characteristics or symptoms of the disease, disorder or condition. Prevention may be considered complete when onset of a disease, disorder or condition has been delayed for a predefined period of time.

Proliferative condition: The term "proliferative condition," as used herein, refers to a disease or disorder associated with cell proliferation. In some embodiments, a proliferative disease or disorder is or comprises cancer. In some embodiments, a proliferative disease or disorder is an inflammatory disease or disorder. In some embodiments, a proliferative disease or disorder is an autoimmune disease or disorder. In some embodiments, a proliferative disease or disorder is a microbial infection (e.g., a bacterial infection).

Reference: As used herein describes a standard or control relative to which a comparison is performed. For example, in some embodiments, an agent, animal, individual, population, sample, sequence or value of interest is compared with a reference or control agent, animal, individual, population, sample, sequence or value. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control.

Risk: as will be understood from context, "risk" of a disease, disorder, and/or condition comprises likelihood that a particular individual will develop a disease, disorder, and/or condition. In some embodiments, risk is expressed as a percentage. In some embodiments, risk is from 0, 1, 2, 3, 4, 5, 6, 7, 8, 9, 10, 20, 30, 40, 50, 60, 70, 80, 90 up to 100%. In some embodiments risk is expressed as a risk relative to a risk associated with a reference sample or group of reference samples. In some embodiments, a reference sample or group of reference samples have a known risk of a disease, disorder, condition and/or event. In some embodiments a reference sample or group of reference samples are from individuals comparable to a particular individual. In some embodiments, relative risk is 0, 1, 2, 3, 4, 5, 6, 7, 8, 9, 10, or more.

Solid form: As is known in the art, many chemical entities (in particular many organic molecules and/or many small molecules) can adopt a variety of different solid forms such as, for example, amorphous forms and/or crystalline forms (e.g., polymorphs, hydrates, solvates, etc). In some embodiments, such entities may be utilized as a single such form (e.g., as a pure preparation of a single polymorph). In some embodiments, such entities may be utilized as a mixture of such forms.

Solid Tumor: As used herein, the term "solid tumor" refers to an abnormal mass of tissue that usually does not contain cysts or liquid areas. Solid tumors may be benign or malignant. Different types of solid tumors are named for the type of cells that form them. Examples of solid tumors are sarcomas, carcinomas, lymphomas, mesothelioma, neuroblastoma, retinoblastoma, etc.

Susceptible to: An individual who is "susceptible to" a disease, disorder, or condition (e.g., influenza) is at risk for developing the disease, disorder, or condition. In some embodiments, an individual who is susceptible to a disease, disorder, or condition does not display any symptoms of the disease, disorder, or condition. In some embodiments, an individual who is susceptible to a disease, disorder, or condition has not been diagnosed with the disease, disorder, and/or condition. In some embodiments, an individual who is susceptible to a disease, disorder, or condition is an individual who has been exposed to conditions associated with development of the disease, disorder, or condition. In some embodiments, a risk of developing a disease, disorder, and/or condition is a population-based risk (e.g., family members of individuals suffering from the disease, disorder, or condition).

Treatment: As used herein, the term "treatment" (also "treat" or "treating") refers to any administration of a therapy that partially or completely alleviates, ameliorates, relieves, inhibits, delays onset of, reduces severity of, and/or reduces incidence of one or more symptoms, features, and/or causes of a particular disease, disorder, and/or condition. In some embodiments, such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

Unit dose: The expression "unit dose" as used herein refers to an amount administered as a single dose and/or in a physically discrete unit of a pharmaceutical composition. In many embodiments, a unit dose contains a predetermined quantity of an active agent. In some embodiments, a unit dose contains an entire single dose of the agent. In some embodiments, more than one unit dose is administered to achieve a total single dose. In some embodiments, administration of multiple unit doses is required, or expected to be required, in order to achieve an intended effect. A unit dose may be, for example, a volume of liquid (e.g., an acceptable carrier) containing a predetermined quantity of one or more therapeutic agents, a predetermined amount of one or more therapeutic agents in solid form, a sustained release formulation or drug delivery device containing a predetermined amount of one or more therapeutic agents, etc. It will be appreciated that a unit dose may be present in a formulation that includes any of a variety of components in addition to the therapeutic agent(s). For example, acceptable carriers (e.g., pharmaceutically acceptable carriers), diluents, stabilizers, buffers, preservatives, etc., may be included as described infra. It will be appreciated by those skilled in the art, in many embodiments, a total appropriate daily dosage of a particular therapeutic agent may comprise a portion, or a plurality, of unit doses, and may be decided, for example, by the attending physician within the scope of sound medical judgment. In some embodiments, the specific effective dose level for any particular subject or organism may depend upon a variety of factors including the disorder being treated and the severity of the disorder; activity of specific active compound employed; specific composition employed; age, body weight, general health, sex and diet of the subject; time of administration, and rate of excretion of the specific active compound employed; duration of the treatment; drugs and/ or additional therapies used in combination or coincidental with specific compound(s) employed, and like factors well known in the medical arts.

The term "$C_{1-6}$ alkyl," as used herein, refers to straight, branched, or cyclic alkyl group. Exemplary $C_{1-6}$ alkyl groups include, but are not limited to, methyl, ethyl, propyl, isopropyl, cyclopropyl, butyl, isobutyl, tert-butyl, cyclobutyl, cyclopropylmethyl, pentyl, isopentyl, neopentyl, cyclopentyl, cyclopropylethyl, hexyl, cyclohexyl, etc.

The term "$C_{1-6}$ alkoxy," as used herein, refers to —O—$C_{1-6}$ alkyl, wherein $C_{1-6}$ alkyl is as described herein.

The term "halogen" and "halo," as used herein, refer to F, Cl, Br, or I.

The singular forms "a", "an", and "the," as used herein and in the claims, include the plural reference unless the context clearly indicates otherwise. Thus, for example, a reference to "a compound" includes a plurality of such compounds.

Compounds

In some embodiments, the present disclosure relates to a compound of formula (I):

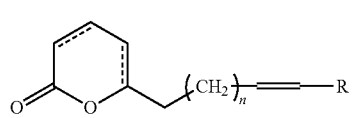

(I)

wherein:
each of ----- is independently absent or a bond;
n is 0-6; and
R is $C_{1-6}$ alkyl, which is optionally substituted 1-3 times by halo, hydroxyl, or $C_{1-6}$ alkoxy.

In some embodiments, a compound of formula (I) is of formula (I-Z):

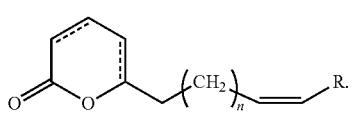

(I-Z)

In some embodiments, a compound of formulas (I) or (I-Z) is of formula (IA):

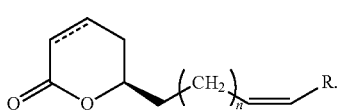

(IA)

In some embodiments, a compound of formulas (I) or (I-Z) is of formula (IB):

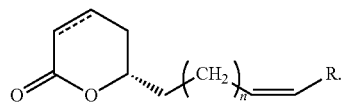

(IB)

In some embodiments, a compound of formulas (I) or (I-Z) is of formula (II):

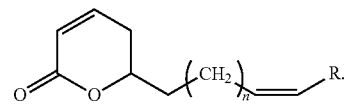

(II)

In some embodiments, a compound of formulas (I), (I-Z), (IA), or (II) is of formula (IIA):

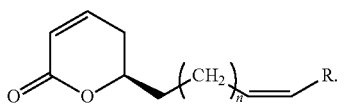

(IIA)

In some embodiments, a compound of formulas (I), (I-Z), (IB), or (II) is of formula (IIB):

(IIB)

In some embodiments, a compound of formulas (I) or (I-Z) is of formula (III):

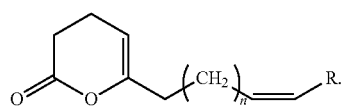

(III)

In some embodiments, a compound of formulas (I) or (I-Z) is of formula (IV):

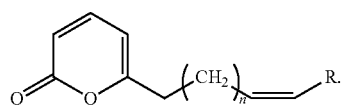

(IV)

In some embodiments, a compound of formula (I) is of formula (I-E):

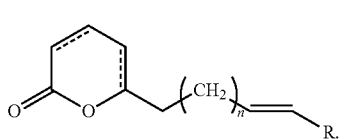

(I-E)

In some embodiments, a compound of formulas (I) or (I-E) is of formula (I'A):

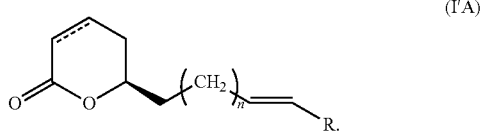

(I'A)

In some embodiments, a compound of formulas (I) or (I-E) is of formula (I'B):

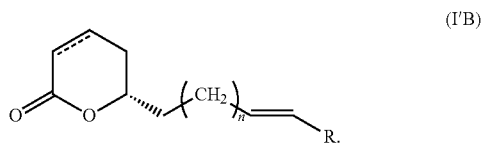

(I'B)

In some embodiments, a compound of formulas (I) or (I-E) is of formula (II'):

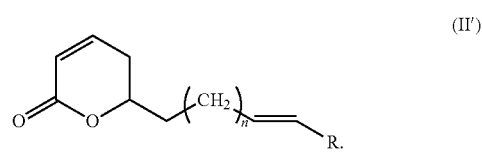

(II')

In some embodiments, a compound of formulas (I), (I-E), (I'A), or (II') is of formula (II'A):

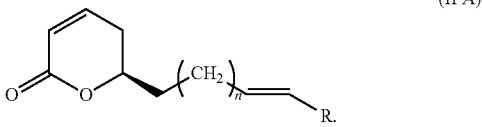

(II'A)

In some embodiments, a compound of formulas (I), (I-E), (I'B), or (II') is of formula (II'B):

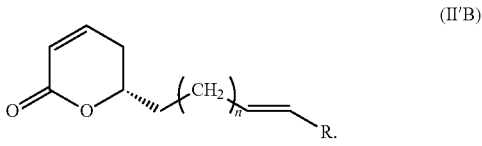

(II'B)

In some embodiments, a compound of formulas (I) or (I-E) is of formula (III'):

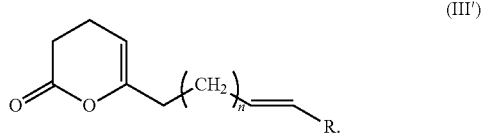

(III')

In some embodiments, a compound of formulas (I) or (I-E) is of formula (IV'):

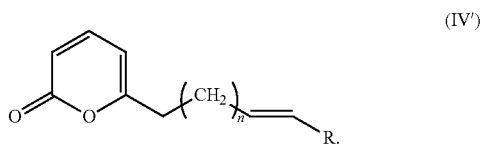

(IV')

In some embodiments of a compound of formulas (I), (I-Z), (IA), (IB), (II), (IIA), (IIB), (III), (IV), (I-E), (I'A), (I'B), (II'), (II'A), (II'B), (III'), or (IV'), n is 0. In some embodiments, n is 1. In some embodiments, n is 2. In some embodiments, n is 3. In some embodiments, n is 4. In some embodiments, n is 5. In some embodiments, n is 6.

In some embodiments of a compound of formulas (I), (I-Z), (IA), (IB), (II), (IIA), (IIB), (III), (IV), (I-E), (I'A), (I'B), (II'), (II'A), (II'B), (III'), or (IV'), R is $C_{1-6}$ alkyl. As described herein, in some embodiments, $C_{1-6}$ alkyl can be a linear, branched, or cyclic alkyl group. In some embodiments, $C_{1-6}$ alkyl is a linear alkyl group. In some embodiments, $C_{1-6}$ alkyl is a branched alkyl group. In some embodiments, $C_{1-6}$ alkyl is a cyclic alkyl group. In some embodiments, R is methyl. In some embodiments, R is ethyl. In some embodiments, R is a linear, branched, or cyclic $C_3$ alkyl. In some embodiments, R is a linear, branched, or cyclic $C_4$ alkyl. In some embodiments, R is a linear, branched, or cyclic $C_5$ alkyl. In some embodiments, R is a linear, branched, or cyclic $C_6$ alkyl.

In some embodiments of a compound of formulas (I), (I-Z), (IA), (IB), (II), (IIA), (IIB), (III), (IV), (I-E), (I'A), (I'B), (II'), (II'A), (II'B), (III'), or (IV'), R is $C_{1-6}$ alkyl, which is substituted 1-3 times by halo, hydroxyl, or $C_{1-6}$ alkoxy. In some embodiments, R is $C_{1-6}$ alkyl which is substituted 1 time by halo, hydroxyl, or $C_{1-6}$ alkoxy. In some embodiments, R is $C_{1-6}$ alkyl which is substituted 2 times by halo, hydroxyl, or $C_{1-6}$ alkoxy. In some embodiments, R is $C_{1-6}$ alkyl which is substituted 3 times by halo, hydroxyl, or $C_{1-6}$ alkoxy. In some embodiments, halo is F. In some embodiments, halo is Cl. In some embodiments, halo is Br. In some embodiments, halo is I. As described herein, $C_{1-6}$ alkoxy refers to —O—$C_{1-6}$ alkyl. In some embodiments, $C_{1-6}$ alkoxy is —O—$C_{1-6}$ alkyl, wherein the $C_{1-6}$ alkyl is a linear alkyl group. In some embodiments, $C_{1-6}$ alkoxy is —O—$C_{1-6}$ alkyl, wherein the $C_{1-6}$ alkyl is a branched alkyl group. In some embodiments, $C_{1-6}$ alkoxy is —O—$C_{1-6}$ alkyl, wherein the $C_{1-6}$ alkyl is a cyclic alkyl group. In some embodiments, $C_{1-6}$ alkoxy is methoxy. In some embodiments, $C_{1-6}$ alkoxy is enthoxy. In some embodiments, $C_{1-6}$ alkoxy is a linear, branched, or cyclic $C_3$ alkyl-O—. In some embodiments, $C_{1-6}$ alkoxy is a linear, branched, or cyclic $C_4$ alkyl-O—. In some embodiments, $C_{1-6}$ alkoxy is a linear, branched, or cyclic $C_5$ alkyl-O—. In some embodiments, $C_{1-6}$ alkoxy is a linear, branched, or cyclic $C_6$ alkyl-O—.

In some embodiments, a compound of formulas (I), (I-Z), or (II) is of formula (V):

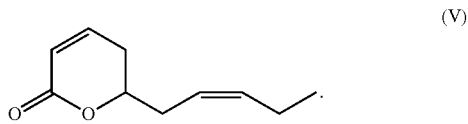

(V)

In some embodiments, a compound of formula (V) is of formula (VA):

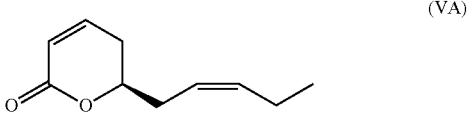

(VA)

(6R)-6-[(2Z)-pent-2-enyl]-5,6-dihydro-2H-pyran-2-one [(R)-(−)-Tuberolactone].

In some embodiments, a compound of formula (V) is of formula (VB):

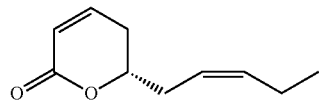
(VB)

(6S)-6-[(2Z)-pent-2-enyl]-5,6-dihydro-2H-pyran-2-one [(R)-(−)-Tuberolactone].

In some embodiments, a compound of formulas (I), (I-E), or (II') is of formula (V'):

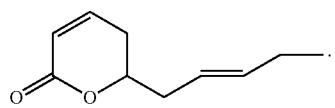
(V')

In some embodiments, a compound of formula (V') is of formula (V'A):

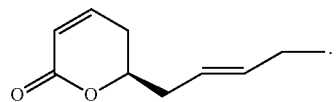
(V'A)

In some embodiments, a compound of formula (V') is of formula (V'B):

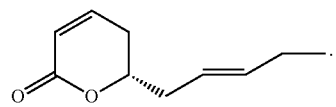
(V'B)

Preparation of Compounds

In some embodiments, a compound of formula (I) may be prepared in whole or in part by chemical synthesis; in some embodiments, a compound of formula (I) prepared in part by chemical synthesis is prepared using semi-synthetic methodologies. In some embodiments, a compound of formula (I) may be prepared by isolation, e.g., from a plant. In some embodiments, a compound of formula (I) may be prepared by isolation from a natural plant; in some embodiments, a compound of formula (I) may be prepared by isolation from a plant that has been engineered (e.g., genetically engineered), cultivated, and/or manipulated by the hand of man.

In some embodiments, provided herein are methods for making a compound of formula (I). In some embodiments, a provided such method comprises a step of obtaining from a plant an extract comprising the compound of formula (I). In some embodiments, the plant is *Gaultheria procumbens*. In some embodiments, the plant is *Polianthes tuberosa* (commonly called Tuberoses or Azucena). In some embodiments, the plant is *Datura stramonium* (commonly called Jimson Weed, Thornapple, or Moon Flower). In some embodiments, the plant is *Osmanthus fragrans Lour.*

In some embodiments, a plant extract comprises alkaloids found in the plant. In some embodiments, methods provided herein comprise one or more steps of fractioning a plant extract.

In some embodiments, methods provided herein comprise assaying one or more plant extracts or fractions thereof, for example to detect bioactivity therein. In some embodiments, methods provided herein comprise a step of detecting and/or confirming presence of detectable antiproliferative activity in one or more plant extracts or fractions thereof. In some embodiments, methods provided herein comprise a step of confirming absence of detectable antiproliferative activity in one or more plant extracts or fractions thereof.

In some embodiments, an antiproliferative activity comprises antibacterial activity. In some embodiments, an antibacterial activity is bioactivity against gram-(+) bacteria. In some embodiments, a gram-(+) bacteria is or comprises a strain of *S. lutea* and/or *B. cereus*. In some embodiments, antibacterial activity is bioactivity against gram-(−) bacteria. In some embodiments, a gram-(−) bacteria is or comprises a strain of *E. aerogenes*.

In some embodiments, an antiproliferative activity comprises cytostatic or cytotoxic activity in one or more tumor cell lines. In some embodiments, the one or more tumor cell lines comprise promyelocytic leukemia HL-60, breast adenocarcinoma MCF-7, and/or lung carcinoma NCI-H292.

Identification and/or Characterization of Compounds and/or Compositions

In some embodiments, provided herein are methods for identifying and/or characterizing an antiproliferative compound and/or a composition comprising it. In some embodiments, such a method comprises steps of testing a plurality of samples, each of which is derived from a plant, for antiproliferative activity; and determining presence and/or level of antiproliferative activity in one or more such samples. In some embodiments, a provided method comprises detecting antiproliferative activity associated with presence and/or level of a compound of formula (I). In some embodiments, a provided method comprises a step of identifying and/or characterizing a particular compound of formula (I) by detecting antiproliferative activity of the compound.

Formulations

In some embodiments, provided herein are compositions comprising a compound of formula (I), and one or more carriers or excipients appropriate for administration to human or animal subjects in accordance with the present disclosure.

In some embodiments, provided herein are methods of manufacturing such a composition, for example by combining one or more appropriate (i.e., pharmaceutically acceptable) carriers or excipients with a compound of formula (I). In some embodiments, the one or more pharmaceutically acceptable carriers or excipients are suitable for oral administration and the mixture is formulated into an oral formulation. In some embodiments, the pharmaceutical composition is a solid dosage form. In some embodiments, the solid dosage form is a tablet, capsule, or lozenge. In some embodiments, the pharmaceutical composition is a liquid dosage form (e.g., a drink).

Remington's Pharmaceutical Sciences, Sixteenth Edition, E. W. Martin (Mack Publishing Co., Easton, Pa., 1980) discloses various carriers used in formulating pharmaceutical compositions and known techniques for the preparation thereof. In some embodiments, provided herein is a pharmaceutical composition comprising a pharmaceutically acceptable amount of a compound provided herein. In some embodiments, amount of active ingredient which can be combined with a carrier material to produce a single dosage form may vary depending upon the host being treated, and/or the particular mode of administration. The amount of active ingredient that can be combined with a carrier material to produce a single dosage form will generally be that amount of the compound which produces a therapeutic effect. Generally, this amount will range from about 1% to about 99% of active ingredient, from about 5% to about 70%, or from about 10% to about 30%.

Wetting agents, emulsifiers, and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. In some embodiments, a formulation provided herein comprises an excipient selected from the group consisting of cyclodextrins, liposomes, micelle forming agents, e.g., bile acids, and polymeric carriers, e.g., polyesters and polyanhydrides; and a compound provided herein. In certain embodiments, a formulation provided herein renders orally bioavailable a compound provided herein.

Methods of preparing such formulations may comprise a step of bringing into association a compound provided herein with one or more pharmaceutically acceptable carriers or excipients, and optionally one or more accessory ingredients. In general, the formulations are prepared by uniformly and intimately bringing into association a compound provided herein with liquid carriers, or finely divided solid carriers, or both, and then, if necessary, shaping the product.

Formulations provided herein suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes, drinks, and the like, each containing a predetermined amount of a compound provided herein as an active ingredient. A compound provided herein may alternatively or additionally be administered as a bolus, electuary or paste.

In solid dosage forms provided herein for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol, glycerol monostearate, and non-ionic surfactants; absorbents, such as kaolin and bentonite clay; lubricants, such as talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-shelled gelatin capsules using such carriers as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made in a suitable machine in which a mixture of the powdered compound is moistened with an inert liquid diluent.

The tablets, and other solid dosage forms of the pharmaceutical compositions provided herein, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compounds provided herein include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations provided herein for rectal or vaginal administration may be presented as a suppository, which may be prepared by mixing one or more compounds provided herein with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations provided herein which are suitable for vaginal administration also include pessaries, tampons, creams, gels, pastes, foams or spray formulations containing such carriers as are known in the art to be appropriate.

Dosage forms for the topical or transdermal administration of a compound provided herein include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to a compound provided herein, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound provided herein, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound provided herein to the body. Dissolving or dispersing the compound in the proper medium can make such dosage forms. Absorption enhancers can also be used to increase the flux of the compound across the skin. Either providing a rate controlling membrane or dispersing the compound in a polymer matrix or gel can control the rate of such flux.

Ophthalmic formulations, eye ointments, powders, solutions and the like, are also contemplated as being within the scope of this invention.

Pharmaceutical compositions provided herein suitable for parenteral administration comprise one or more compounds provided herein in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers, which may be employed in the pharmaceutical compositions provided herein include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

The compositions provided herein may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, for example in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

Drug-eluting forms include coated or medicated stents and implantable devices. Drug-eluting stents and other devices may be coated with a compound or pharmaceutical preparation and may further comprise a polymer designed for time-release.

In some embodiments, a compound or pharmaceutical preparation is administered orally. In some embodiments, the compound or pharmaceutical preparation is administered intravenously. In some embodiments, a compound is attached via a cleavable linker to a solid support that is administered with a catheter. Alternative routes of administration include sublingual, intramuscular, and transdermal administrations.

When the compounds provided herein are administered as pharmaceuticals, to humans and animals, they can be given per se or as a pharmaceutical composition containing, for example, 0.1% to 99.5%, or 0.5% to 90%, of active ingredient in combination with a pharmaceutically acceptable carrier.

The compounds provided herein may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories.

The compounds provided herein may be administered to humans and other animals for therapy by any suitable route of administration, including orally, nasally, as by, for example, an aerosol, a spray, rectally, intravaginally, parenterally, intracisternally and topically, as by powders, ointments or drops, including buccally and sublingually.

Regardless of the route of administration selected, the compounds provided herein, which may be used in a suitable hydrated form, and/or the pharmaceutical compositions as provided herein, are formulated into pharmaceutically-acceptable dosage forms by conventional methods known to those of skill in the art.

Actual dosage levels of the active ingredients in the pharmaceutical compositions provided herein may be varied so as to obtain an amount of the active ingredient that is effective to achieve the desired therapeutic response for a particular patient, composition, and mode of administration, without being toxic to the patient.

In some embodiments, a selected dosage level will depend upon a variety of factors including the activity of the particular compound provided herein, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can determine and prescribe the effective amount of the pharmaceutical composition required. For example, the physician or veterinarian could start doses of the compounds provided herein in the pharmaceutical composition at levels lower than that required to achieve the desired therapeutic effect and then gradually increasing the dosage until the desired effect is achieved.

In some embodiments, a compound or pharmaceutical composition provided herein is provided to a subject chronically. Chronic treatments include any form of repeated administration for an extended period of time, such as repeated administrations for one or more months, between a month and a year, one or more years, or longer. In some embodiments, a chronic treatment involves administering a compound or pharmaceutical composition provided herein repeatedly over the life of the subject. In some embodiments, chronic treatments involve regular administrations, for example one or more times a day, one or more times a week, or one or more times a month. In general, a suitable dose such as a daily dose of a compound provided herein will be that amount of the compound that is the lowest dose effective to produce a therapeutic effect. Such an effective dose will generally depend upon the factors described herein. Generally doses of the compounds provided herein for a patient, when used for the indicated effects, will range from about 0.0001 to about 100 mg per kg of body weight per day. In some embodiments, the daily dosage will range from 0.001 to 50 mg of compound per kg of body weight. In some embodiments, the daily dosage will range from 0.01 to 10 mg of compound per kg of body weight. However, lower or higher doses can be used. In some embodiments, the dose administered to a subject may be modified as the physiology of the subject changes due to age, disease progression, weight, or other factors.

If desired, the effective daily dose of the active compound may be administered as two, three, four, five, six, or more sub-doses administered separately at appropriate intervals throughout the day, optionally, in unit dosage forms.

While it is possible for a compound provided herein to be administered alone, it is preferable to administer the compound as a pharmaceutical formulation (composition) as described herein.

The compounds provided herein may be formulated for administration in any convenient way for use in human or veterinary medicine, by analogy with other pharmaceuticals.

Uses

In some embodiments, provided herein is a method for treating a proliferative condition in need thereof, comprising administering to the subject a therapeutically effective amount of a compound of formula (I) (e.g., in a composition as described herein).

In some embodiments, the proliferative disease or disorder is cancer. In some embodiments, the cancer is a hematological malignancy. In certain embodiments, the cancer is characterized by presence of one or more solid tumors.

Exemplary cancers that may be treated using the compounds and compositions provided herein include adrenal cancer, acinic cell carcinoma, acoustic neuroma, acral lentiginous melanoma, acrospiroma, acute eosinophilic leukemia, acute erythroid leukemia, acute lymphoblastic leukemia, acute megakaryoblastic leukemia, acute monocytic leukemia, acute promyelocytic leukemia, adenocarcinoma, adenoid cystic carcinoma, adenoma, adenomatoid odontogenic tumor, adenosquamous carcinoma, adipose tissue neoplasm, adrenocortical carcinoma, adult T-cell leukemia/lymphoma, aggressive NK-cell leukemia, AIDS-related lymphoma, alveolar rhabdomyosarcoma, alveolar soft part sarcoma, ameloblastic fibroma, anaplastic large cell lymphoma, anaplastic thyroid cancer, angioimmunoblastic T-cell lymphoma, angiomyolipoma, angiosarcoma, astrocytoma, atypical teratoid rhabdoid tumor, B-cell chronic lymphocytic leukemia, B-cell prolymphocytic leukemia, B-cell lymphoma, basal cell carcinoma, biliary tract cancer, bladder cancer, blastoma, bone cancer, Brenner tumor, Brown tumor, Burkitt's lymphoma, breast cancer, brain cancer, carcinoma, carcinoma in situ, carcinosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer, Degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy-associated T-cell lymphoma, esophageal cancer, fetus in fetu, fibroma, fibrosarcoma, follicular lymphoma, follicular thyroid cancer, ganglioneuroma, gastrointestinal cancer, germ cell tumor, gestational choriocarcinoma, giant cell fibroblastoma, giant cell tumor of the bone, glial tumor, glioblastoma multiforme, glioma, gliomatosis cerebri, glucagonoma, gonadoblastoma, granulosa cell tumor, gynandroblastoma, gallbladder cancer, gastric cancer, hairy cell leukemia, hemangioblastoma, head and neck cancer, hemangiopericytoma, hematological malignancy, hepatoblastoma, hepatosplenic T-cell lymphoma, Hodgkin's lymphoma, non-Hodgkin's lymphoma, invasive lobular carcinoma, intestinal cancer, kidney cancer, laryngeal cancer, lentigo maligna, lethal midline carcinoma, leukemia, leydig cell tumor, liposarcoma, lung cancer, lymphangioma, lymphangiosarcoma, lymphoepithelioma, lymphoma, acute lymphocytic leukemia, acute myelogenous leukemia, chronic lymphocytic leukemia, liver cancer, small cell lung cancer, non-small cell lung cancer, MALT lymphoma, malignant fibrous histiocytoma, malignant peripheral nerve sheath tumor, malignant triton tumor, mantle cell lymphoma, marginal zone B-cell lymphoma, mast cell leukemia, mediastinal germ cell tumor, medullary carcinoma of the breast, medullary thyroid cancer, medulloblastoma, melanoma, meningioma, merkel cell cancer, mesothelioma, metastatic urothelial carcinoma, mixed Mullerian tumor, mucinous tumor, multiple myeloma, muscle tissue neoplasm, mycosis fungoides, myxoid liposarcoma, myxoma, myxosarcoma, nasopharyngeal carcinoma, neurinoma, neuroblastoma, neurofibroma, neuroma, nodular melanoma, ocular cancer, oligoastrocytoma, oligodendroglioma, oncocytoma, optic nerve sheath meningioma, optic nerve tumor, oral cancer, osteosarcoma, ovarian cancer, Pancoast tumor, papillary thyroid cancer, paraganglioma, pinealoblastoma, pineocytoma, pituicytoma, pituitary adenoma, pituitary tumor, plasmacytoma, polyembryoma, precursor T-lymphoblastic lymphoma, primary central nervous system lymphoma, primary effusion lymphoma, primary peritoneal cancer, prostate cancer, pancreatic cancer, pharyngeal cancer, pseudomyxoma peritonei, renal cell carcinoma, renal medullary carcinoma, retinoblastoma, rhabdomyoma, rhabdomyosarcoma, Richter's transformation, rectal cancer, sarcoma, Schwannomatosis, seminoma, Sertoli cell tumor, sex cord-gonadal stromal tumor, signet ring cell carcinoma, skin cancer, small blue round cell tumors, small cell carcinoma, soft tissue sarcoma, somatostatinoma, soot wart, spinal tumor, splenic marginal zone lymphoma, squamous cell carcinoma, synovial sarcoma, Sezary's disease, small intestine cancer, squamous carcinoma, stomach cancer, T-cell lymphoma, testicular cancer, thecoma, thyroid cancer, transitional cell carcinoma, throat cancer, urachal cancer, urogenital cancer, urothelial carcinoma, uveal melanoma, uterine cancer, verrucous carcinoma, visual pathway glioma, vulvar cancer, vaginal cancer, Waldenstrom's macroglobulinemia, Warthin's tumor, and Wilms' tumor.

In some embodiments, a proliferative disease or disorder is a benign proliferative disorder. Such benign proliferative disorders include, but are not limited to, benign soft tissue tumors, bone tumors, brain and spinal tumors, eyelid and orbital tumors, granuloma, lipoma, meningioma, multiple endocrine neoplasia, nasal polyps, pituitary tumors, prolactinoma, pseudotumor cerebri, seborrheic keratoses, stomach polyps, thyroid nodules, cystic neoplasms of the pancreas, hemangiomas, vocal cord nodules, polyps, and cysts, Castleman disease, chronic pilonidal disease, dermatofibroma, pilar cyst, pyogenic granuloma, and juvenile polyposis syndrome.

In some embodiments, a proliferative disease or disorder is inflammatory disease. In some embodiments, a proliferative disease or disorder is autoimmune disease.

Examples of autoimmune and inflammatory diseases which may be treated using the compounds and compositions described herein include, but are not limited to, inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholecystitis, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, Type I diabetes, septic shock, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, Guillain-Barre syndrome, Behcet's disease, scleracierma, mycosis fungoides, acute inflammatory responses (such as acute respiratory distress syndrome and ischemia/reperfusion injury), and Graves' disease. In some embodiments, the compounds and compositions provided herein can be used for treating systemic inflammatory response syndromes such as LPS-induced endotoxic shock and/or bacteria-induced sepsis.

In some embodiments, a proliferative disease or disorder is microbial infection. In some embodiments, the microbial infection is bacterial infection. In some embodiments, a bacterial infection is an infection with gram-(+) bacteria; in some embodiments, a bacterial infection is an infection with gram-(−) bacteria.

Exemplary bacterial infections which may be treated by the compounds and compositions provided herein include infections caused by one or more of the following bacteria: *Pseudomonas* (e.g., *P. aeruginosa, P. paucimobilis, P. putida, P. fluorescens,* and *P. acidovorans*), *Burkholderia* (e.g., *B. pseudomallei, B. cepacia, B. cepacia* complex, *B. dolosa, B. fungorum, B. gladioli, B. multivorans, B. vietnamiensis, B. pseudomallei, B. ambifarict, B. andropogonis, B. anthina, B. brasilensis, B. caledonica, B. caribensis, B. caryophylli*), *Staphylococcus* (e.g., *S. aureus, S. auricularis, S. carnosus, S. epidermidis, S. lugdunensis*), Methicillin-resistant *Staphylococcus aureus* (MRSA), *Streptococcus* (e.g., *Streptococcus pneumoniae*), *Escherichia coli, Enterobacter, Serratia, Haemophilus, Yersinia pestis, Mycobacterium* (e.g., nontuberculous mycobacterium, *M. abscessus, M. chelonae, M. bolletii, M. tuberculosis, M. avium* complex (MAC) (*M. avium* and *M. intracellulare*), *M. kansasii, M. xenopi, M. marinum, M. ulcerans,* or *M. fortuitum* complex (*M. fortuitum* and *M. chelonae*)).

In some embodiments, compounds and/or pharmaceutical compositions can be employed in accordance with the present invention in combination therapies. In some embodiments, such combination therapy comprises administration of such a compound and/or composition in combination with one or more other therapies (e.g., with one or more other therapeutics or procedures). In some embodiments, a particular combination of therapies (therapeutics or procedures) to be employed in a combination regimen in accordance with the present disclosure will take into account compatibility of the desired therapeutics and/or procedures and the desired therapeutic effect to be achieved.

It will also be appreciated, in some embodiments, combined therapies employed may be selected to achieve a desired effect for the same disorder (for example, an compound herein may be administered concurrently with another antiproliferative [e.g., anticancer] agent), or they may be selected to achieve different effects (e.g., control of any adverse effects).

For example, in some embodiments, therapies that may be used in combination with the compounds and compositions herein may include surgery, radiotherapy (gamma-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), to name a few. Additionally, the present invention also encompasses the use of certain cytotoxic or anticancer agents currently in clinical trials and which may ultimately be approved by the FDA (including, but not limited to, epothilones and analogues thereof and geldanamycins and analogues thereof). For a more comprehensive discussion of updated cancer therapies see, www.nci.nih.gov and The Merck Manual, nineteenth Ed. 2011, the entire contents of which are hereby incorporated by reference.

In some embodiments, compounds and/or compositions as described herein may be used in combination with one or more anti-inflammatory therapies, including but not limited to, drug therapy, and administration with anti-inflammatory cytokines. Exemplary anti-inflammatory drugs include, but are not limited to, antihistamines, non-steroidal anti-inflammatory agents (NSAIDs), eicosanoid receptor antagonists, cytokine antagonists, monoclonal antibodies, 3-hydroxymethylglutaryl-coenzyme A (HMG-CoA) reductase inhibitors, and corticosteroids (see, for example, Goodman and Gilman's The Pharmacological Basis of Therapeutics). Antihistamines fall generally under three broad classes, according to the histamine receptor subtype they antagonize and display specificity for. Histamine H1 receptors are primarily responsible for the anti-inflammatory response, while H2 receptors are limited to gastric acid secretion. Histamine H1 receptor antagonists include, but are not limited to, carbinoxamine, clemastine, diphenhydramine, dimenhydrinate, pyrilamine, tripelennamine, chlorpheniramine, brompheniramine, chlorcyclizine, acrivastine, promethazine, as well as piperazines such as astemizole, levocabastine, hydroxyzine, cyclizine, cetirizine, meclizine, loratadine, fexofenadine, and terfenadine. NSAIDs include the salicylate derivatives, para-aminophenol derivatives, indole and indene acetic acids, heteroaryl acetic acids, arylpropionic acids, anthranilic acids (also known in the art as fenamates), enolic acids, and alkanones. Salicylate derivates include aspirin, sodium salicylate, choline magnesium trisalicylate, salsalate, diflunisal, salicylsalicylic acid, sulfasalazine, and olsalazine, but are not limited to these drugs. Para-aminophenol derivates are exemplified by acetaminophen. Indomethacin, sulindac, and etodolac comprise indole and indene acetic acids, while heteroaryl acetic acids include tolmetin, diclofenac, and ketorolac. Examples of arylpropionic acids include ibuprofen, naproxen, flurbiprofen, ketoprofen, fenoprofen, and oxaprozin. Fenamates, include but are not limited to mefenamic acid and meclofenamic acid. Some examples of enolic acids include the oxicams piroxicm and tenoxicam, and pyrazolidinediones such as phenylbutazone and oxyphenthatrazone. Alkanones can comprise nabumetone. Eicosanoid receptor antagonists include, but are not limited to, leukotriene modifiers, which can act as leukotriene receptor antagonists by selectively competing for LTD-4 and LTE-4 receptors. These compounds include, but are not limited to, zafirlukast tablets, zileuton tablets, and montelukast. Zileuton tablets function as 5-lipoxygenase inhibitors. Cytokine antagonists can comprise anti-TNF.alpha. antibodies, and fusion proteins of the ligand binding domain of the TNF.alpha. receptor and the Fc portion of human immunoglobulin G1. Other cytokine antagonists include recombinant human interleukin-1 receptor antagonist, recombinant human IFN.alpha., recombinant human IFN.beta., IL-4 muteins, soluble IL-4 receptors, immunosuppressants (such as tolerizing peptide vaccine), anti-IL-4 antibodies, IL-4 antagonists, anti-IL-5 antibodies, soluble IL-13 receptor-Fc fusion proteins, anti-IL-9 antibodies, CCR3 antagonists, CCR5 antagonists, VLA-4 inhibitors, downregulators of IgE, among others. Corticosteroids cause a decrease in the number of circulating lymphocytes as a result of steroid-induced lysis of lymphocytes, or by alterations in lymphocyte circulation patterns (Kuby, J. (1998) In: Immunology 3.sup.rd Edition W.H. Freeman and Company, New York; Pelaia, G. et al. Life Sci. 72(14): 1549-61). Corticosteroids affect the regulation of nuclear factor .kappa.B (NF-.kappa.B) by inducing the upregulation of an inhibitor of NF-.kappa.E known as I.kappa.B, which sequesters NF-.kappa.B in the cytoplasm and prevents it from transactivating pro-inflammatory genes in the nucleus. Corticosteroids also reduce the phagocytic ability of macrophages and neutrophils, as well as reducing chemotaxis. Examples of corticosteroids are alclometasone, amcinonide, beclomethasone, betamethasone, clobetasol, clocortolone, cortisol, hydrocortisone, prednisolone, and prednisone, but are not limited to these examples. Additional anti-inflammatory cytokines include, but not limited to, interleukin-4 (IL-4), interleukin-10 (IL-10), interleukin-13 (IL-13), interleukin-16 (IL-16), interleukin-1 receptor antagonist (IL-1ra), interferon .alpha. (IFN.alpha.), transforming growth factor-.beta. (TGF-.beta.), among others. The cytokines may be administered together or separately in combination with the compounds and compositions provided herein.

In some embodiments, compounds and/or compositions as described herein may be used be used in combination with an anti-pathogen therapy. Exemplary anti-pathogen therapies include antibiotics, antivirals, fungicides, nematicides, and parasiticides, or any other biocide. Parasiticides are agents that kill parasites directly and can be used in combination with the compounds and compositions described herein. Exemplary parasiticides include but are not limited to albendazole, amphotericin B, benznidazole, bithionol, chloroquine HCl, chloroquine phosphate, clindamycin, dehydroemetine, diethylcarbamazine, diloxanide furoate, eflornithine, furazolidaone, glucocorticoids, halofantrine, iodoquinol, ivermectin, mebendazole, mefloquine, meglumine antimoniate, melarsoprol, metrifonate, metronidazole, niclosamide, nifurtimox, oxamniquine, paromomycin, pentamidine isethionate, piperazine, praziquantel, primaquine phosphate, proguanil, pyrantel pamoate, pyrimethaminesulfonamides, pyrimethanmine-sulfadoxine, quinacrine HCl, quinine sulfate, quinidine gluconate, spiramycin, stibogluconate sodium (sodium antimony gluconate), suramin, tetracycline, doxycycline, thiabendazole, tinidazole, trimethroprim-sulfamethoxazole, and tryparsamide some of which are used alone or in combination with others. Other anti-pathogen therapeutics useful in combination with the compounds and compositions provided herein include, but are not limited to, any one or more of the following: agent which reduces the activity of or kills a microorganism and includes but is not limited to Aztreonam; Chlorhexidine Gluconate; Imidurea; Lycetamine; Nibroxane; Pirazmonam Sodium; Propionic Acid; Pyrithione Sodium; Sanguinarium Chloride; Tigemonam Dicholine; Acedapsone; Acetosulfone Sodium; Alamecin; Alexidine; Amdinocillin; Amdinocillin Pivoxil; Amicycline; Amifloxacin; Amifloxacin Mesylate; Amikacin; Amikacin Sulfate; Aminosalicylic acid; Aminosalicylate sodium; Amoxicillin; Amphomycin; Ampicillin; Ampicillin Sodium; Apalcillin Sodium; Apramycin; Aspartocin; Astromicin Sulfate; Avilamycin; Avoparcin; Azithromycin; Azlocillin; Aziocillin Sodium; Bacanipicillin-Hydrochloride; Bacitracin; Bacitracin Methylene Disalicylate;

Bacitracin Zinc; Bambennycins; Benzoylpas Calcium; Berythromycin; Betamicin Sulfate; Biapenem; Biniramycin; Biphenamine Hydrochloride; Bispyrithione Magsulfex; Butikacin; Butirosin Sulfate; Capreomycin Sulfate; Carbadox; Carbenicillin Disodium; Carbenicillin Indanyl Sodium; Carbenicillin Phenyl Sodium; Carbenicillin Potassium; Carumonam Sodium; Cefaclor, Cefadroxil; Cefamandole; Cefamandole Nafate; Cefamandole Sodium; Cefaparole; Cefatrizine; Cefazaflur Sodium; Cefazolin; Cefazolin Sodium; Cefbuperazone; Cefdinir; Cefepime; Cefepime Hydrochloride; Cefetecol; Cefixime; Cefinenoxime Hydrochloride; Cefmetazole; Cefmetazole Sodium; Cefonicid Monosodium; Cefonicid Sodium; Cefoperazone Sodium; Ceforanide; Cefotaxime Sodium; Cefotetan; Cefotetan Disodium; Cefotiam Hydrochloride; Cefoxitin; Cefoxitin Sodium; Cefpimizole; Cefpimizole Sodium; Cefpiramide; Cefpiramide Sodium; Cefpirome Sulfate; Cefpodoxime Proxetil; Cefprozil; Cefroxadine; Cefsulodin Sodium; Ceftazidime; Ceftibuten; Ceftizoxime Sodium; Ceftriaxone Sodium; Cefuroxime; Cefuroxime Axetil; Cefuroxime Pivoxetil; Cefuroxime Sodium; Cephacetrile Sodium; Cephalexin; Cephalexin Hydrochloride, Cephaloglycin; Cephaloridine; Cephalothin Sodium; Cephapirin Sodium; Cephradine; Cetocycline Hydrochloride; Cetophenicol; Chloramphenicol; Chloramphenicol Palmitate; Chloramphenicol Pantothenate Complex; Chloramphenicol Sodium Succinate; Chlorhexidine Phosphanilate; Chloroxylenol; Chlortetracycline Bisulfate; Chlortetracycline Hydrochloride; Cinoxacin; Ciprofloxacin; Ciprofloxacin Hydrochloride; Cirolemycin; Clarithromycin; Clinafloxacin Hydrochloride; Clindamycin; Clindamycin Hydrochloride; Clindamycin Palmitate Hydrochloride; Clindamycin Phosphate; Clofazimine; Cloxacillin Benzathine; Cloxacillin Sodium; Cloxyquin; Colistimethate Sodium; Colistin Sulfate; Coumermycin; Coumermycin Sodium; Cyclacillin; Cycloserine; Dalfopristin; Dapsone; Daptomycin; Demeclocycline; Demeclocycline Hydrochloride; Demecycline; Denofungin; Diaveridine; Dicloxacillin; Dicloxacillin Sodium; Dihydrostreptomycin Sulfate; Dipyrithione; Dirithromycin; Doxycycline; Doxycycline Calcium; Doxycycline Fosfatex; Doxycycline Hyclate; Droxacin Sodium; Enoxacin; Epicillin; Epitetracycline Hydrochloride; Erythromycin; Erythromycin Acistrate; Erythromycin Estolate; Erythromycin Ethylsuccinate; Erythromycin Gluceptate; Erythromycin Lactobionate; Erythromycin Propionate; Erythromycin Stearate; Ethambutol Hydrochloride; Ethionamide; Fleroxacin; Floxacillin; Fludalanine; Flumequine; Fosfomycin; Fosfomycin Tromethamine; Fumoxicillin; Furazolium Chloride; Furazolium Tartrate; Fusidate Sodium; Fusidic Acid; Gentamicin Sulfate; Gloximonam; Gramicidin; Haloprogin; Hetacillin; Hetacillin Potassium; Hexedine; Ibafloxacin; Imipenem; Isoconazole; Isepamicin; Isoniazid; Josamycin; Kanamycin Sulfate; Kitasamycin; Levofuraltadone; Levopropylcillin Potassium; Lexithromycin; Lincomycin; Lincomycin Hydrochloride; Lomefloxacin; Lomefloxacin Hydrochloride; Lomefloxacin Mesylate; Loracarbef; Mafenide; Meclocycline; Meclocycline Sulfosalicylate; Megalomicin Potassium Phosphate; Mequidox; Meropenem; Methacycline; Methacycline Hydrochloride; Methenamine; Methenamine Hippurate; Methenamine Mandelate; Methicillin Sodium; Metioprim; Metronidazole Hydrochloride; Metronidazole Phosphate; Mezlocillin; Mezlocillin Sodium; Minocycline; Minocycline Hydrochloride; Mirincamycin hydrochloride; Monensin; Monensin Sodium; Nafcillin Sodium; Nalidixate Sodium; Nalidixic Acid; Natamycin; Nebramycin; Neomycin Palmitate; Neomycin Sulfate; Neomycin Undecylenate; Netilmicin Sulfate; Neutramycin; Nifuradene; Nifuraldezone; Nifuratel; Nifuratrone; Nifurdazil; Nifurimide; Nifurpirinol; Nifurquinazol; Nifurthiazole; Nitrocycline; Nitrofurantoin; Nitromide; Norfloxacin; Novobiocin Sodium; Ofloxacin; Ormetoprim; Oxacillin Sodium; Oximonam; Oximonam Sodium; Oxolinic Acid; Oxytetracycline; Oxytetracycline Calcium; Oxytetracycline Hydrochloride; Paldimycin; Parachlorophenol; Paulomycin; Pefloxacin; Pefloxacin Mesylate; Penamecillin; Penicillin G Benzathine; Penicillin G Potassium; Penicillin G Procaine; Penicillin G Sodium; Penicillin V; Penicillin V Benzathine; Penicillin V Hydrabamine; Penicillin V Potassium; Pentizidone Sodium; Phenyl Aminosalicylate; Piperacillin Sodium; Pirbenicillin Sodium; Piridicillin Sodium; Pirlimycin Hydrochloride; Pivampicillin Hydrochloride; Pivampicillin Pamoate; Pivampicillin Probenate; Polymyxin B Sulfate; Porfiromycin; Propikacin; Pyrazinamide; Pyrithione Zinc; Quindecamine Acetate; Quinupristin; Racephenicol; Ramoplanin; Ranimycin; Relomycin; Repromicin; Rifabutin; Rifametane; Rifamexil; Rifamide; Rifampin; Rifapentine; Rifaximin; Rolitetracycline; Rolitetracycline Nitrate; Rosaramicin; Rosaramicin Butyrate; Rosaramicin Propionate; Rosaramicin Sodium Phosphate; Rosaramicin Stearate; Rosoxacil; Roxarsone; Roxithromycin; Sancycline; Sanfetrinem Sodium; Sarmoxicillin; Sarpicillin; Scopafungin; Sisomicin; Sisomicin Sulfate; Sparfloxacin; Spectinomycin Hydrochloride; Spiramycin; Stallimycin Hydrochloride; Steffunycin; Streptomycin Sulfate; Streptonicozid; Sulfabenz: Sulfabenzamide; Sulfacetamide; Sulfacetamide Sodium; Sulfacytine; Sulfadiazine; Sulfadiazine Sodium; Sulfadoxine; Sulfalene; Sulfamerazine; Sulfameter; Sulfamethazine; Sulfamethizole; Sulfamethoxazole; Sulfamonomethoxine; Sulfamoxole; Sulfanilate Zinc; Sulfanitran; Sulfasalazine; Sulfasomizole; Sulfathiazole; Sulfazamet; Sulfisoxazole; Sulfisoxazole Acetyl; Sulfisoxazole Diolamine; Sulfomyxin; Sulopenem; Sultamicillin; Suncillin Sodium; Talampicillin Hydrochloride; Teicoplanin; Temafloxacin Hydrochloride; Temocillin; Tetracycline; Tetracycline Hydrochloride; Tetracycline Phosphate Complex; Tetroxoprim; Thiamphenicol; Thiphencillin Potassium; Ticarcillin Cresyl Sodium: Ticarcillin Disodium; Ticarcillin Monosodium; Ticlatone; Tiodonium Chloride; Tobramycin; Tobramycin Sulfate; Tosufloxacin; Trimethoprim; Trimethoprim Sulfate; Trisulfapyrimidines; Troleandomycin; Trospectomycin Sulfate; Tyrothricin; Vancomycin; Vancomycin Hydrochloride; Virginiamycin; Zorbamycin; Difloxacin Hydrochloride; Lauryl Isoquinolinium Bromide; Moxalactam Disodium; Ornidazole; Pentisomicin; and Sarafloxacin Hydrochloride.

EXAMPLES

Example 1. Preparation of (6R)-6-[(2Z)-pent-2-enyl]-5,6-dihydro-2H-pyran-2-one [(R)-(−)-Tuberolactone]

235 mg alkaloids were extracted from 750 g leaves from the plant, *Gaultheria procumbens* (also called American wintergreen, teaberry, or boxberry). Fractionation of the crude extract was guided by antimicrobial activity against several gram-(+) and gram-(−) strains: *Enterobacter aerogenes* (Gram-negative rods), *Bacillus cereus* (Gram-positive rods), and *Sarcina lutea* (Gram-positive rods), using the paper disk diffusion method (Barry, A. L.; Thornsbery, C. *Identification for Clinical Microbiology*, 4$^{th}$ ed.; Washington, D.C., 1985; p 978) supplied within the Science Kit & Boreal Laboratories Antibiotic Effects Kit. The SK Antibiotics Effect Kit uses "Easygel" instead of agar dishes. Each paper disk (6 mm) containing approximately 100 μg of the extract was placed directly onto an Easygel plate, which had been freshly inoculated with either a gram-(+) or (−) strain. In addition, a standard antibiotic disk (30 μg of either penicillin, tetracycline, or chloramphenicol supplied within Science Kit & Boreal Laboratories Antibiotic Effects Kit) as well as a blank disk (with only solvent) were placed on the freshly inoculated Easygel plate. After 24 h of incubation at 28° C., the inhibition zones were observed for the bioactive fractions. 45 mg (6R)-6-[(2Z)-pent-2-enyl]-5,6-dihydro-2H-pyran-2-one [(R)-(−)-Tuberolactone] were isolated (MW. 166.0989 g/mol).

One- and two-dimensional homo- and hetero-nuclear spectral data were obtained to characterize and identify the structure of the compound, for example, 1H and 13C one-dimensional NMR, HMQC, HMBC, NOESY, and GCOSEY data were obtained in both CDCl3 and DMSO-d6. Gross structure was determined via above NMR techniques as well as relative and absolute stereochemistry via polarimetry.

Example 2. Anticancer Activity of (6R)-6-[(2Z)-pent-2-enyl]-5,6-dihydro-2H-pyran-2-one [(R)-(−)-Tuberolactone]

The human tumor cell lines used were HL-60 (promyelocytic leukemia), MCF-7 (breast adenocarcinoma) and NCI-H292 (lung carcinoma). The cells were obtained from Rio de Janeiro Cell Bank (RJ, Brazil). Cancer cells were maintained in RPMI 1640 medium or DMEN supplemented with 10% fetal bovine serum, 2 mM glutamine, 100 U/mL penicillin, 100 μg/mL streptomycin at 37° C. with 5% $CO_2$. Cytotoxicity of (6R)-6-[(2Z)-pent-2-enyl]-5,6-dihydro-2H-pyran-2-one [(R)-(−)-Tuberolactone] against the three tumor cell lines was assessed using the 3-(4,5-dimethyl-2-thiazolyl)-2,5-diphenyl-2H tetrazolium bromide (MTT) (Sigma Aldrich Co., St. Louis, Mo., USA) reduction assay. Tumor cells were plated in 96-well plates ($10^5$ cells/mL for adherent cells or $3\times10^5$ cells/mL for Leukemia). (6R)-6-[(2Z)-pent-2-enyl]-5,6-dihydro-2H-pyran-2-one [(R)-(−)-Tuberolactone] in DMSO (0.3-25 μg/mL) were added to each well and incubated for 72 h. Control groups received the same amount of DMSO. After 69 h of treatment, 25 μL of MTT (5 mg/mL) was added. Three hours later, the MTT formazan product was dissolved in 100 μL of DMSO. Absorbance was measured at 595 nm in plate spectrophotometer (Varioskan Flash, Thermo Scientific). Doxorubicin (0.01-5 μg/mL in DMSO) was used as positive control. $IC_{50}$ values and their 95% confidence intervals for two different experiments were obtained by non linear regression using Graphpad Prism version 5.0 for Windows (GraphPad Software, San Diego, Calif., USA).

Results

TABLE 1

$IC_{50}$ values and 95% confidence interval of (R)-(−)-tuberolactone on tumor cell lines. Results are in g/mL.

| Sample | $IC_{50}$, 95% confidence intervals g/mL (μM) | | |
|---|---|---|---|
| | HL-60 | MCF-7 | NCI-H292 |
| Tuberolactone | 4.4 (26) 3.5-5.6 | 6.4 (38.5) 5.3-7.7 | 5.9 (35.5) 4.9-7.2 |

TABLE 1-continued $IC_{50}$ values and 95% confidence interval of (R)-(−)-tuberolactone on tumor cell lines. Results are in g/mL.

| Sample | $IC_{50}$, 95% confidence intervals g/mL (μM) | | |
|---|---|---|---|
| | HL-60 | MCF-7 | NCI-H292 |
| Doxorubicin | 0.02 (0.36) 0.01-0.02 | 0.30 (0.5) 0.20-0.50 | 0.20 (0.36) 0.10-0.50 |

Example 3. Antibacterial Activity of (6R)-6-[(2Z)-pent-2-enyl]-5,6-dihydro-2H-pyran-2-one [(R)-(−)-Tuberolactone]

Using the paper disk diffusion method as described above, antibacterial activity of (6R)-6-[(2Z)-pent-2-enyl]-5,6-dihydro-2H-pyran-2-one [(R)-(−)-Tuberolactone] was confirmed against gram-(+) (*S. lutea* and *B. cereus* strains) and gram-(−) (*E. aerogenes* strain) bacteria strains.

While some embodiments are illustrated in the examples, it is apparent that they may be altered to provide other embodiments of the instant disclosure. Therefore, it will be appreciated that the scope of the invention is to be defined by the appended claims rather than by the specific embodiments that have been represented by way of example.

The invention claimed is:
1. A method for inhibiting cell proliferation, comprising administering to a subject a therapeutically effective amount of a compound of formula (VA):

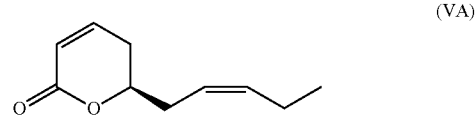

(VA)

wherein:
the cell is a gram-(+) or gram-(−) bacteria cell selected from the group consisting of *S. lutea*, *B. cereus*, and *E. aerogenes*, or a cancer cell selected from the group consisting of a leukemia cell, a breast cancer cell, and a lung cancer cell.

2. The method of claim 1, wherein the cell is a gram-(+) or gram-(−) bacteria cell selected from the group consisting of *S. lutea*, *B. cereus*, and *E. aerogenes*.

3. The method of claim 1, wherein the bacteria cell is a gram-(+) bacteria cell selected from *S. lutea* and *B. cereus*.

4. The method of claim 1, wherein the bacteria cell is *S. lutea*.

5. The method of claim 1, wherein the bacteria cell is *B. cereus*.

6. The method of claim 1, wherein the bacteria cell is *E. aerogenes*.

7. The method of claim 1, wherein the cell is a cancer cell selected from the group consisting of a leukemia cell, a breast cancer cell, and a lung cancer cell.

8. The method of claim 1, wherein the cell is a leukemia cell.

9. The method of claim 1, wherein the cell is a breast cancer cell.

10. The method of claim 1, wherein the cell is a lung cancer cell.

* * * * *